United States Patent [19]

Meadows et al.

[11] Patent Number: 5,747,025
[45] Date of Patent: *May 5, 1998

[54] BIOLOGICAL CONTROL OF PESTS

[75] Inventors: Martin Paul Meadows, Brighton; Deborah June Ellis, Bognor Regis; Paul Jarrett, Littlehampton, all of United Kingdom

[73] Assignee: Agricultural Genetics Co., Ltd., Cambridge, England

[ * ] Notice: The term of this patent shall not extend beyond the expiration date of Pat. No. 5,501,852.

[21] Appl. No.: 473,907

[22] Filed: Jun. 7, 1995

Related U.S. Application Data

[62] Division of Ser. No. 365,188, Dec. 28, 1994, Pat. No. 5,501,852, which is a continuation of Ser. No. 883,330, May 14, 1992, abandoned.

[30] Foreign Application Priority Data

May 14, 1991 [GB] United Kingdom .................. 9110391

[51] Int. Cl.$^6$ .................................................. A01N 63/00
[52] U.S. Cl. ................................. 424/93.461; 435/252.5; 435/832
[58] Field of Search ........................ 435/252.5, 832, 435/170; 424/93.461; 530/825

[56] References Cited

U.S. PATENT DOCUMENTS

| | | | |
|---|---|---|---|
| 4,277,564 | 7/1981 | Johnson | 435/242 |
| 4,695,462 | 9/1987 | Barnes et al. | 424/195.1 |
| 4,915,943 | 4/1990 | Gago et al. | 424/93 |
| 4,948,734 | 8/1990 | Edwards et al. | 435/252.5 |
| 4,990,332 | 2/1991 | Payne et al. | 424/93 |
| 5,039,523 | 8/1991 | Payne et al. | 424/93 |
| 5,061,489 | 10/1991 | Bernier et al. | 424/93 |
| 5,063,055 | 11/1991 | Burges et al. | 424/93 |
| 5,080,897 | 1/1992 | Gonzalez, Jr. et al. | 424/93 |
| 5,164,180 | 11/1992 | Payne et al. | 424/93 L |
| 5,169,629 | 12/1992 | Payne et al. | 424/93 L |
| 5,211,946 | 5/1993 | Payne et al. | 424/93 L |
| 5,322,687 | 6/1994 | Donovan et al. | 424/93 A |
| 5,356,623 | 10/1994 | Von Tersch et al. | 424/93.2 |
| 5,501,852 | 3/1996 | Meadows et al. | 424/93.461 |

FOREIGN PATENT DOCUMENTS

| | | |
|---|---|---|
| 178151 | 4/1986 | European Pat. Off. . |
| 0 303 379 | 2/1989 | European Pat. Off. . |

OTHER PUBLICATIONS

Dulmage, H.T. et al., "Journal of Invertebrate Pathology," vol. 15, pp. 15–20, 1970.

Johnson, D.E., "FEMS Microbiology Letters," vol. 43, pp. 121–125, 1987.

McGaughey, WM. H. et al., "J. Econ. Entomol.," vol. 80(6), pp. 1122–1126, 1987.

Höfte et al., Microbiological Reviews, Jun. 1989, pp. 242–255 vol. 53, No. 2.

Pana–Beratlief, Z., AN. I.C.P.P., vol. 8, pp. 213–224,1972.

Solanes, R. et al., Facultad de Ciencias Agrarias, vol. 20(1), pp. 3–10, 1974.

Tompkins, G. et al., ACS Symposium Series, vol. 432, pp. 9–13 (chap. 2), 1990.

Khovrychev, M.P. et al., Microbiology, vol. 56(3), pp. 341–345, 1987.

Sneh, B. et al., Entomophaga, vol. 26(2), pp. 179–190, 1981.

Dulmage et al "Coprecipitation With Lactose As A Means Of Recovering The Spore–Crystal Complex Of *Bacillus Thuringiensis* "; Journal of Invertebrate Pathology, 15, 15–20.

*Primary Examiner*—Irene Marx
*Attorney, Agent, or Firm*—Wenderoth, Lind & Ponack

[57] ABSTRACT

This invention relates to a strain of *Bacillus thuringiensis* M200, a sample of which has been deposited under the accession number NCIMB 40385, or a variant, derivative or mutant thereof having entomocidal activity against lepidopterous pests. The invention also relates to the use of the said strain for control of insect pests.

10 Claims, No Drawings

BIOLOGICAL CONTROL OF PESTS

REFERENCE TO PRIOR APPLICATIONS

This application is a division of application Ser. No. 08/365,188 filed Dec. 28, 1994 (now U.S. Pat. No. 5,501,852), which is a continuation of now abandoned U.S. Ser. No. 07/883,330 filed May 14, 1992.

This invention relates to biological methods of pest control and more particularly to methods and compositions utilising Bacillus thuringiensis for the control of agricultural and horticultural pests.

BACKGROUND OF THE INVENTION

*Bacillus thuringiensis* is a spore forming bacterium which has long been known to kill insects and many hundreds of isolates (strains) of this species have been listed. The properties of individual *B. thuringiensis* strains and their activity against insect pests vary widely from strain to strain.

BRIEF DESCRIPTION OF THE INVENTION

We have now isolated a new strain of *Bacillus thuringiensis* which has been found to be highly active against agricultural and horticultural pests including those of the family Pieridae, including *Pieris brassicae* (Large White Butterfly), and pests of the family Yponomeutidae, including *Plutella xylostella* (Diamond-back moth). The activity of the new strain, designated M200, is several-fold greater towards the above pests than many known strains of *B. thuringiensis* including those used commercially and those under current development which have been described in the literature.

DETAILED DESCRIPTION OF THE INVENTION

The present invention comprises *Bacillus thuringiensis* strain M200 a sample of which has been deposited under the Budapest Treaty with the National Collection of Industrial and Marine Bacteria under Accession No. NCIMB 40385, on 20 Mar. 1991.

The present invention also comprises the use of *B. thuringiensis* strain M200 for the control of pests which affect plants. Accordingly the invention comprises a method of pest control in which agricultural and horticultural produce are protected against pests by application of this new strain to the growing plants or other horticultural products or to their growing locations. The invention also comprises compositions containing the new strain and formulated for agricultural or horticultural application. The invention is applicable also to variants, mutants, recombinants, and derivatives of the new strain which are similarly biologically effective. Such derivatives include those obtained by genetic manipulation.

The strain *Bacillus thuringiensis* M200 has the H-serotype 3a3b. When grown for 24 h at 30° C. on nutrient agar the colonies are circular, entire, convex, off-white, have a ground glass appearance and a diameter of 2–8 mm. The vegetative cells are Gram-positive, aerobic rods producing sub-terminal spores towards the end of the growth cycle. At the same time as sporulation, a parasporal, proteinaceous crystal is produced which is approximately the same size as the spore.

A biochemical profile of M200 on standard substrates (API ZONE test strip) is shown below. HD1 is the commercially available strain and GC91 is the subject of our UK patent 2,165,261.

| | Strain Code No | | |
|---|---|---|---|
| Reaction | M200 | HD1 | GC91 |
| $NO_3$ (nitrate reduction) | + | − | + |
| TRP (indole production) | − | − | − |
| GLU (glucose acidification) | − | − | − |
| ADH (arginine dihydrolase) | + | − | + |
| URE (urease) | − | − | − |
| ESC (esculin hydrolysis) | + | − | + |
| GEL (gelatine hydrolysis) | + | + | + |
| PNPG (β-galactosidase) | − | − | − |
| GLU (glucose assimilation) | + | + | + |
| ARA (arabinose assimilation) | − | − | − |
| MNE (mannose assimilation) | − | − | − |
| MAN (mannitol assimilation) | − | − | − |
| NAG (N-acetyl glucosamine assimilation) | + | + | + |
| MAL (maltose assimilation) | + | + | + |
| GNT (gluconate assimilation) | + | + | + |
| CAP (caprate assimilation) | − | − | − |
| ADI (adipate assimilation) | − | − | − |
| MLT (malate assimilation) | + | + | + |
| CIT (citrate assimilation) | − | − | − |
| PAC (phenylacetate assimilation) | − | − | − |

*B. thuringiensis* can be produced on a large scale by submerged fermentation using processes such as those described by Lee et al in Microbial Biomass (1979, A. H. Rose (ed). Academic Press) pp 91–114. Typical growth media may contain any of the following ingredients in various combinations: fishmeal, cottonseed meal, soybean meal, molasses, diammonium phosphate, starch. During production by fermentation, after normal growth of *Bacillus thuringiensis*, the mother cells lyse and release the spores and crystals into the growth medium. The spores and crystals may be harvested by centrifugation or filtration, spray drying, vacuum drying, or a method of precipitation, such as the lactose coprecipitation technique as reported by Dulmage et al (Journal of Invertebrate Pathology, 15, 15–20, 1970). The resulting spore-crystal complex is stable for long periods and can be formulated into a product suitable for application to crops.

The invention also includes the use of delta endotoxins derived from the above-mentioned new organism. The invention provides an entomocidal substance derived from *Bacillus thuringiensis* strain M200, or from a derivative or mutant thereof. In one embodiment the entomocidal substance is a spore-crystal complex. The spore-crystal complex or the composition containing it may be administered to the plants or crops to be protected together with certain other insecticides or chemicals without loss or potency.

It is possible to kill the spores in the spore-crystal (e.g. by gamma irradiation), or to avoid producing spores by use of an asporogenous crystaliferous mutant, thereby producing a non-viable product. A non-viable product may be advantageous in certain circumstances where it is desired to prevent the spread of bacteria for aesthetic reasons or to avoid causing disease in beneficial insects. However, non-viable products are generally not as active as those containing live spores and as a further disadvantage there is the increased cost of killing the spores.

The invention further provides an entomocidal substance derived from *Bacillus thuringiensis* strain M200 (NCIMB 40385) or a derivative or mutant thereof, or an entomocidal substance as defined above together with an agricultural adjuvant such as a carrier, diluent, surfactant or application-promoting adjuvant. The composition may also contain a further biologically active compound selected from fertilisers, micronutrient donors, plant growth preparations, herbicides, insecticides, fungicides, bactericides, nematicides and molluscicides and mixtures thereof. The composition may comprise from 0.1 to 99% by weight of *Bacillus thuringiensis* M200 or the derivative or mutant thereof, or the entomocidal substance; from 1 to 99.9% by weight of a solid or liquid adjuvant and from 0 to 25% by weight of a surfactant.

The invention in addition provides a method of combatting pests which comprises applying to the pests or to their environment an entomocidally effective amount of *Bacillus thuringiensis* strain M200, or a derivative or mutant thereof, or an entomocidal substance as defined above, or a composition containing said strain, derivative, mutant or substance.

*Bacillus thuringiensis* strain M200 or the compositions containing it may be administered to the plants or crops to be protected together with certain other insecticides or chemicals without loss of potency. It is compatible with most other commonly used agricultural spray materials but should not be used in extremely alkaline spray solutions. It may be administered as a dust, a suspension, a wettable powder or in any other material form suitable for agricultural application.

The invention furthermore relates to a method of treating crops which comprises applying an entomocidally effective amount of *B. thuringiensis* M200, or a composition thereof.

*Bacillus thuringiensis* M200, is normally applied in the form of compositions and can be applied to the crop area to be treated, simultaneously or in succession, with further biologically active compounds. These compounds may be both fertilizers or micronutrient donors or other preparations that influence plant growth. They may also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, takifiers, binders or fertilizers.

The formulations, i.e., the compositions, preparations or mixtures containing *B. thuringiensis* M200 as an active ingredient or combinations thereof with other active ingredients, and, where appropriate, a solid or liquid adjuvant, are prepared in known manner e.g. by homogeneously mixing and/or grinding the active ingredients with extenders e.g. solvents, solid carriers and in some cases surface-acting compounds (surfactants).

Suitable solvents are: aromatic hydrocarbons, preferably the fractions containing 8 to 12 carbon atoms, e.g. xylene mixtures or substituted napthalenes, phthalates such as dibutylphthalate or dioctylphthalate, aliphatic hydrocarbons such as cyclohexane or paraffins, alcohols and glycols, such as cyclohexanone, strongly polar solvents such as N-methyl-2-pyrrolidone, dimethylsulfoxide or dimethylformamide as well as vegetable oils or epoxidized vegetable oils such as epoxidized coconut oil or soybean oil; or water.

The solid carriers used e.g. for dusts and dispersable powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the active ingredients to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds. Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids. More frequently, however, so-called synthetic surfactants are used, especially fatty sulfonates, fatty sulfates, sulfonated benzimidazole derivatives or alkylarylsulfonates.

The fatty sulfonates or sulfates are usually in the forms of alkali metal salts, alkaline earth metal salts or unsubstituted or substituted ammonium salts and generally contain a $C_8$–$C_{22}$ alkyl radical which also includes the alkyl moiety of acyl radicals, e.g. the sodium or calcium salt of lignosulfonic acid, or dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkyl-arylsufonates are the sodium, calcium or triethanolamine salts of dodecylbenzenesulfonic acid, dibutylnapththalenesulfonic acid or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$ alkyl radical and, as further substituents, lower unsubstituted or halogenated alkyl, benzyl or hydroxyl-lower alkyl radicals. The salts are preferably in the form of halides, methylsulfates or ethylsulfates e.g. stearyltrimethylammonium chloride or benzyldi-(2-chloroethyl)ethylammonium bromide.

The surfactants customarily employed in the art of formulation are described e.g. in "McCutcheon's Detergents and Emulsifiers Annual", MC Publishing Corp, Ridgewood, N.J., 1979; Dr Helmut Stache, "Tensid Taschenbuch" (Handbook of Surfactants), Carl Hanser Verlag, Munich/Vienna.

The entomocidal compositions usually contain 0.1 to 99%, preferably 0.1 to 95% of *Bacillus thuringiensis* M200, or combination thereof with other active ingredients, 1 to 99.9% of a solid or liquid adjuvant and 0 to 25%, preferably 0.1 to 20%, of a surfactant.

Whereas commercial products are preferably formulated as concentrates, the end user will normally employ dilute formulations of substantially lower concentration.

The compositions may also contain further ingredients, such as stabilizers, antifoams, viscosity regulators, binders, tackifiers as well as fertilizers or other active ingredients in order to obtain special effects.

EXAMPLES

The invention will now be further described with reference to experimental and field test data obtained in comparative testing of isolate M200 and of other *B. thuringiensis* isolates.

Example 1

Large Scale Culture of *B. thuringiensis*

*Bacillus thuringiensis* strain M200 can be cultured on a large scale as follows:

The strain is maintained in lyophilized ampoules, which are used as stocks for inoculating the strain onto agar slopes. The slopes are incubated for 1 to 5 days at 20° to 40° C., preferably 25° to 33° C., following which they are used to inoculate shaken flasks containing an aqueous culture medium. The flasks are shaken at a temperature of 20° to 40° C. preferably 30° C. for 1 to 5 days; preferably 1 to 2 days (this vegetative growth stage can be repeated optionally at least once in a separate flask), and used to inoculate a preculture fermenter containing an aqueous cultivating medium. The fermentation medium containing the inoculate is stirred at and aerated at a temperature of 20° to 40° C., preferably 30° to 35° C., (optionally this preculture fermentation stage can be repeated at least once in a separate larger container), before being introduced at 2 to 20 per cent by weight of the incubating liquor into a production fermenter, containing an aqueous cultivating medium. The medium is stirred and aerated at a temperature of 20° to 40° C., preferably 30° to 35° C. until the *Bacillus thuringiensis* M200 broth is harvested when sporulation and crystal production in the production fermenter reaches a maximum. The agar and broth used for preparation of inocula for the preculture fermenter should contain at least one nitrogen source, at least one carbon source and at least one salt, preferably peptone, glucose and at least one salt. The fermentation media should contain at least one nitrogen source (e.g. peptone, yeast extract, corn steep liquor, soya bean meal, cotton seed meal, fishmeal), at least one carbohydrate source (e.g. glucose, lactose, sucrose, starch or raw material rich in these constituents) and at least one mineral salt. The nitrogen and carbohydrate should be balanced to exhaust as near as possible simultaneously. Cultures can be concentrated after harvesting by centrifugation to produce a slurry containing a spore/crystal concentrate. The concentrate can be converted into a dry powder by spray-drying.

Example 2

Insect Bioassays

The activity of *B. thuringiensis* strain M200 against the insects *Pieris brassicae* and *Plutella xylostella* was compared in bioassays with *B. thuringiensis* strains GC91 which is the subject of our UK patent 2,165,261 and the commercially available strain HD1. Bacterial powders were prepared as described in Example 1 and activities against insects assayed by the addition of a series of concentrations of the powders to artificial diets on which the larvae fed. For *P. brassicae* the semi-synthetic diet of David, W. A. L. and Gardiner, R. O. C. (1965), [Nature, London 207, No 4999, pp 882–883] was used. All larvae used in bioassays were neonates. Mortality was recorded after 5 days with the temperature maintained at 25° C. For *P. xylostella* the same semi-synthetic diet was used, except that all antibiotics were omitted, but all larvae used in bioassays were at the beginning of the third instar. Mortality was recorded after 5 days with the temperature maintained at 25° C.

*B. thuringiensis* strain GC91 was included in all batches of bioassays as an internal standard. It can be seen from the results expressed in Table 1 that the activity of *B. thuringiensis* strain M200 towards *P. brassicae* is 10 to 16-fold greater than that of strain GC91 and 2.5 to 4-fold greater than that of HD1. Similarly the activity of *B. thuringiensis* strain M200 towards *P. xylostella* is 13-fold greater than that of strain GC91 and 16-fold greater than that of HD1.

Example 3

Formulation Examples for solid active ingredients of *Bacillus thuringiensis* M200 or combinations thereof with other active Ingredients (throughout, percentages are by weight)

| 1. Wettable powders | a) | b) | c) |
|---|---|---|---|
| *Bacillus thuringiensis* M200 | 25% | 50% | 75% |
| sodium lignosulfonate | 5% | 5% | — |
| sodium laurylsulfate | 3% | — | 5% |
| sodium diisobutylnapthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

*Bacillus thuringiensis* M200, is thoroughly mixed with the adjuvants and the mixture is thoroughly ground in a suitable mill, affording wettable powders which can be diluted with water to give suspensions of the desired concentration.

| 2. Emulsifiable concentrate | |
|---|---|
| *Bacillus thuringiensis* M200 | 10% |
| octylphenol polyethylene glycol ether (4–5 moles of ethylene oxide) | |
| calcium dodecylbenzenesulfonate | 3% |
| castor oil polyglycol ether (36 moles of ethylene oxide) | 3% |
| | 4% |
| cyclohexanone | 30% |
| xylene mixture | 50% |

Emulsions of any required concentration can be obtained from this concentrate by dilution with water.

| 3. Dusts | a) | b) |
|---|---|---|
| Bacillus thuringiensis M200 | 5% | 8% |
| talcum | 95% | — |
| kaolin | — | 92% |

Ready for use dusts are obtained by mixing the active ingredient with the carriers and grinding the mixture in a suitable mill.

| 4. Extruder granulate | |
|---|---|
| Bacillus thuringiensis M200 | 10% |
| sodium lignosulfonate | 2% |
| carboxymethylcellulose | 1% |
| kaolin | 87% |

The active ingredient or combination is mixed and ground with the adjuvants and the mixture is subsequently moistened with water. The mixture is extruded, granulated and then dried in a stream of air.

| 5. Coated granulate | |
|---|---|
| Bacillus thuringiensis M200 | 3% |
| polyethylne glycol (mol. wt. 200) | 3% |
| kaolin | 94% |

The finely ground active ingredient or combination is uniformly applied in a mixer to the kaolin moistened with polyethylene glycol. Non-dusty coated granulates are obtained in this manner.

| 6. Suspension Concentrate | |
|---|---|
| Bacillus thuringiensis M200 | 40% |
| ethylene glycol | 10% |
| nonylphenol polyethylene glycol ether (15 moles of ethylene oxide) | 6% |
| sodium lignosulfonate carboxymethylcellulose | 10% |
| 37% aqueous formaldehyde solution silicone oil in the form of a | 0.2% |
| 75% aqueous emulsion | 0.8% |
| water | 32% |

The finely ground active ingredient or combination is intimately mixed with the adjuvants giving a suspension concentrate from which suspensions of any desired concentration can be obtained by dilution with water.

Example 4
Field Trials

B. thuringiensis strains M200 and GC91 were prepared as wettable powder formulations using the method described in Example 3. These formulations contained 25% and 50% by weight of strains M200 or GC91 respectively. The two strains were compared for control of P. xylostella, Pieris rapae and Trichoplusia ni in a series of field trials on cabbages. The results, expressed as percentage control of insect larvae, are summarized in Table 2. These results clearly indicate that, in the field, strain M200 is at least twice as active as strain GC91 on a weight for weight basis. The wettable powder used in these trials represents only one example of an effective formulation, preparation of many other effective formulations will be known to those skilled in the art.

TABLE 1

Activity of B. thuringiensis strain M200 against Pieris brassicae and Plutella xylostella

| Isolate | LC$_{50}$ of Isolate[1] (Fiducial limits) | LC$_{50}$ of GC91[1] (Fiducial limits) | Potency[2] |
|---|---|---|---|
| *P. brassicae* | | | |
| M200 | 0.16 (0.07–0.26) | 1.64 (1.1–2.49) | 10 |
| M200 (replicate) | 0.096 (0.038–0.17) | 1.54 (0.92–2.73) | 16 |
| HD1 | 0.40 (0.30–0.50) | 1.60 (1.05–2.50) | 4 |
| *P. xylostella* | | | |
| M200 | 0.07 (0.014–0.15) | 0.93 (0.63–1.36) | 13 |
| HD1 | 1.32 (0.95–1.83) | 1.08 (0.75–1.54) | 0.8 |

[1]LC$_{50}$ is expressed as the dose of B. thuringiensis powder (ug per g diet) which gave 50% mortality.
[2]Potency is expressed as the ratio of LC$_{50}$ of the standard isolate (GC91) to LC$_{50}$ of the test isolate (M200 or HD1).

TABLE 2

Activity of B. thuringiensis strain M200 in field trials against Plutella xylostella, Pieris rapae and Trichoplusia ni on cabbage

| Strain | Application Rate (lb/acre) | P. xylostella | % Control T. ni | P. rapae |
|---|---|---|---|---|
| M200[1] | 0.25 | 84.3 | — | 100.0 |
| | 0.50 | 93.9 | — | 97.0 |
| | 1.00 | 95.0 | 83.5 | 100.0 |
| | 1.50 | — | 93.7 | — |
| GC91[2] | 1.00 | 81.9 | 83.5 | 100.0 |
| | 1.50 | 71.0 | 93.7 | 100.0 |

[1]Wettable powder containing 25% B. thuringiensis strain M200 and prepared as described in Example 3.
[2]Wettable powder containing 50% B. thuringiensis strain GC91 and prepared as described in Example 3.

We claim:

1. An entomocidal substance obtained from a culture of the strain Bacillus thuringiensis M200, NCIMB 40385, or from the culture of a mutant thereof having all of the identifying characteristics of strain NCIMB 40385, wherein said entomocidal substance is the spore-crystal complex.

2. An entomocidal composition comprising as the active ingredient (a) a biologically pure culture of the strain Bacillus thuringiensis M200, NCIMB 40385, or a mutant thereof having all of the identifying characteristics of the strain NCIMB 40385, or (b) an isolated entomocidal substance obtained from a culture of the strain Bacillus thuringiensis M200, NCIMB 40385, or from the culture of a mutant thereof having all of the identifying characteristics of the strain NCIMB 40385, wherein said entomocidal substance is the spore-crystal complex, in combination with a carrier, diluent surfactant or application-promoting adjuvant.

3. The compositions of claim 2, wherein the active ingredient is the spore-crystal complex.

4. The composition of claim 2, wherein the active ingredient is 25 to 75% by weight of (a) or (b) and the composition further contains from 0 to 5% by weight of sodium lignosulfate, from 0 to 5% by weight of sodium laurylsulfate, from 0 to 10% by weight of sodium diisobutylnaphthalene sulfonate, from 0 to 2% by weight of octylphenol polyethylene glycol ether, from 5 to 10% by weight of highly dispersed silic acid; and from 0 to 62% by weight of kaolin.

5. The composition of claim 4, wherein the active ingredient is the spore-crystal complex.

6. The composition of claim 2 further comprising a substance selected from the group consisting of fertilizers, micronutrient donors, plant growth preparations, herbicides, insecticides, fungicides, bactericides, nematicides, molluscicides and mixtures thereof.

7. The composition of claim 2 comprising 0.1 to 99% by weight of (a) or (b), from 1 to 99.9% by weight of a solid or liquid adjuvant; and from 0 to 25% of a surfactant.

8. The composition of claim 7, wherein the active ingredient is the spore-crystal complex.

9. A method of combatting lepidopterous insect pests affecting plants which comprises contacting said insect pests or the locus of said insect pests with an insect-controlling effective amount of an entomocidal composition comprising as the active ingredient (a) a biologically pure culture of the strain *Bacillus thuringiensis* M200, NCIMB 40385, or a mutant thereof having all of the identifying characteristics of the strain NCIMB 40385, or (b) an isolated entomocidal substance obtained from a culture of the strain *Bacillus thuringiensis* M200, NCIMB 40385, or from the culture of a mutant thereof having all of the identifying characteristics of NCIMB 450385, wherein said entomocidal substance is the spore-crystal complex in combination with a carrier, diluent, surfactant or application-promoting adjuvant.

10. A method of claim 9, wherein the active ingredient is the spore-crystal complex.

* * * * *